United States Patent [19]
Ferrari et al.

[11] 3,944,582
[45] Mar. 16, 1976

[54] CARBAMATES OF ERGOLINES
[75] Inventors: Giorgio Ferrari; Jiri Jan Krepinsky, both of Milan, Italy
[73] Assignee: Simes Societa Italiana Medicinali e Sintetici S.p.A., Milan, Italy
[22] Filed: May 20, 1974
[21] Appl. No.: 471,701

[30] Foreign Application Priority Data
  May 23, 1973  Italy .................................. 24513/73

[52] U.S. Cl. .............................. 260/285.5; 424/261
[51] Int. Cl.² ............... C07D 457/06; C07D 457/08
[58] Field of Search ................................. 260/285.5

[56] References Cited
UNITED STATES PATENTS
3,704,233  11/1972  Eich et al. ........................ 260/285.5

FOREIGN PATENTS OR APPLICATIONS
243,993    12/1965   Austria ............................ 260/285.5
1,047,164  12/1966   United Kingdom .............. 260/285.5

Primary Examiner—Richard J. Gallagher
Assistant Examiner—Mary C. Vaughn
Attorney, Agent, or Firm—Cushman, Darby & Cushman

[57] ABSTRACT

Ergoline carbamates are disclosed, which have proven to be effective spasmolytic and vasodilatory drugs. They are derivatives of D-6-methyl-8β-(methanol)-9,10-didehydroergoline (also called lysergol). Three convenient methods for their preparation are also disclosed. The toxicity of these compounds is extremely low.

26 Claims, No Drawings

CARBAMATES OF ERGOLINES

In the present invention the preparation and the use are described of novel compounds having the general formula:

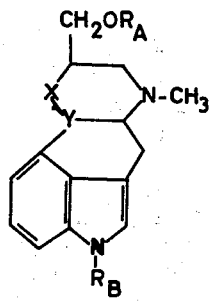

wherein the radicals $R_A$ and $R_B$ have the following meaning: $R_A$ is the group

wherein $R_1$ and $R_2$, in their turn, are H, aliphatic or alicyclic alkyls, straight or branched, containing from 1 to 12 carbon atoms, phenyl, alkylbenzene or a phenethyl substituted in the aromatic ring and/or the aliphatic chain, with alkyls, hydroxyls, methoxyls, aminic groups, dioxymethylene groups, in variable number and combination as clearly shown in the part concerning the examples, $R_B$ is a hydrogen atom, an alkyl group with a number of carbon atoms comprised between 1 and 5 or the radical —$(CH_2)_2$ $R_3$, (wherein $R_3$ is CN, $CONHR_4$, and $R_4$ is —$(CH_2)_{1\text{-}5}$ $CH_3$, or —$(CH_2)_{1\text{-}7}$). Lastly, x⎯y, still in the general formula is the radical —$CH_2$—$CH{<}$ or the unsaturated radical —$CH = C{<}$.

As the starting product there is used D-6-methyl-8β-(methanol)-9,10-didehydroergoline (known also with the name of lysergol) having the general formula above wherein $R_A = R_B = H$, x⎯y = —$CH=C{<}$, as obtained according to the method disclosed in the Italian Patent No. 945,968 of 29.9.1971, or by using general chemical methods of the known art using various precursors, or reduction products of the double bond of lysergol using the conventional methods in which $R_A=R_B=H$, x⎯y = —$CH_2$—$CH{<}$, that is, D-6-methyl-8β-(methanol)-ergoline, or D-6-methyl-8β-(methanol)-10β-ergoline. For the manufacture of these compounds it has been found that the methods reported in the following are the most suitable.

According to the first method (A) the compound of general formula (I) (wherein

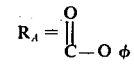

and $R_B$ has the above indicated meaning), obtained by reaction of the compound of general formula I (wherein $R_A$=H) with phenyl chloroformate

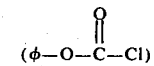

in piridine or another inert solvent with an addition of a tertiary organic base (such as a trialkylamine), is reacted with one of the compounds of general formula $HNR_1R_2$ ($R_1$ and $R_2$ have the same meaning indicated above) in excess in an anhydrous aprotic polar solvent.

More particularly, in its essential lines, the preparation method A is carried out as follows and as shown in the pattern reported below:

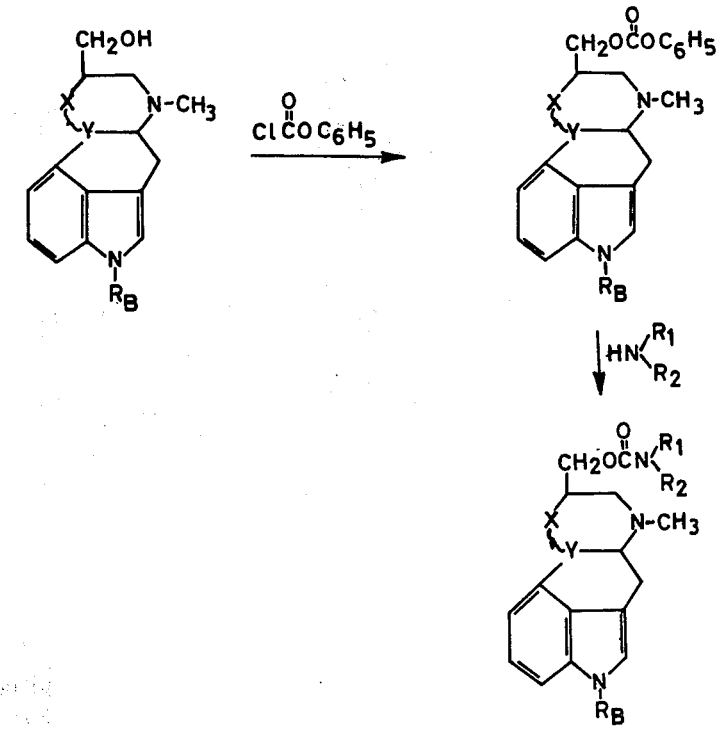

The substance of general formula (I)

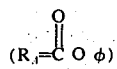

(one equivalent) is dissolved in an anhydrous aprotic polar solvent (for example $(CH_3)_2$ N—COH, $(CH_3)_2$ SO: $[(CH_3)_2N]_3PO$) so as to obtain a concentration of 15% — 20% approx. according to the solubilities and this solution is supplemented, with stirring and at room temperature, with a 10% solution (approx.) in one of the solvents indicated above containing 2.15 molar equivalent of a compound $HNR_1R_2$. The mixture is maintained stirred at a temperature comprised between 60°C and 80°C for a period of from 2 to 26 hours. As the conversion is completed, the mixture is poured in water and ice; a semisolid product precipitates, which can be (a) filtered and crystallized from an appropriate solvent, or (b) the aqueous phase can be extracted with chloroform, the combined extracts washed with water and dried over $Na_2SO_4$, etc., and evaporated to dryness in a vacuo. The residue, as directly crystallized after having been dissolved in an appropriate solvent (or solvent mixture) or, also, prior to crystallization, can be purified with appropriate conventional methods, such as chromatography, treatment with activated carbon, and so forth.

According to the method (B) the corresponding isocyanate is used, $O=C=N—R_2$ and the procedure is as follows A suspension of one equivalent of the substance of general formula (I) ($R_A=H$) in anhydrous benzene, toluene, xylene or acetonitrile, is refluxed with 1.2 molar equivalents of substituted isocyanate $O=C=NR_2$ during 3 to 5 hours. Thereafter, the as formed precipitate is collected on a filter and purified as above. The reaction pattern is as follows:

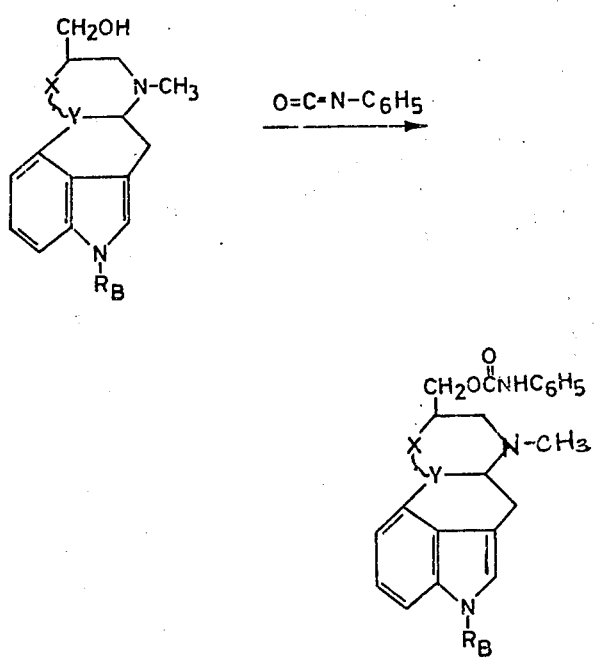

As already outlined for the compounds of the present invention having the formula I X—Y is $—CH_2—CH\subset$, or $—CH=C\subset$ In the case in which the starting compound already contains the second of said groups, the methods (A) and (B) indicated above can either be preceded or followed by a hydrogenation step, according to whether in the final product the presence of a double bond is desired or not.

In the case in which in the starting compound X—Y is $\supset C=C\subset$, the methods (A) and (B) can either be preceded or followed by a particular hydrogenation step as illustrated hereinafter.

The compound (X—Y = $\supset C = C\subset$) in a 5% solution in an alcohol (preferably ethanol), containing 10% of glacial acetic acid is hydrogenated by using catalyst of the platinum type or palladated carbon type, palladated calcium or strontium carbonate type, and the like. The hydrogenation can be carried out under atmospherical pressures or slightly above, up to 3 to 4 atmospheres.

After having attained the theoretically calculated consumption (usually during 1 to 10 hours), the catalyst is collected on a filter and the alcohol is evaporated off in a vacuo (20 to 40 millimeters of mercury, abs.). The residue is diluted with thrice its volume of water and the solution neutralized with sodium bicarbonate. The as formed precipitate is thoroughly washed with water and purified by using the conventional methods, such as for example crystallization, chromatography and the like.

In the list to follow there are reported the examples of the novel compounds as prepared according to the present invention.

I.

D-6-methyl-8β-(carbamoylmethyl)-9,10-didehydroergoline.

Melting point (m.p. 182°–183°C (benzene); $[\alpha]_D^{20}$ + 33.2° (c=1, $C_5H_5N$), UV (MeOH) 311 nm ($\epsilon$ =7830), 241 nm (flex, $\epsilon$ =17,200), IR (KBr): 1603, 1720 cm$^{-1}$.

For $C_{17}H_{19}N_3O_2$ (297.4) Calcd. C% = 68.67; H% = 6.44; N% = 14.14; Found: C, 68.55; H, 6.30; n, 14.15

II.

D-6-methyl-8β-sec.butylaminocarbonyloxymethyl)-9,10-didehydroergoline.

m.p. 197°–199°C (benzene) ; $[\beta]_D^{20} = +46.7°$ (c=1, $C_5H_5N$), UV (MeOH 312 nm ($\epsilon$ =8500); IR (KBr) ; 1705, 1602 cm$^{-1}$, (CHCl$_3$): 1712,1602 cm$^{-1}$.

For $C_{21}H_{27}N_3O_2$ (353.5) Calcd. C% = 71.36 ; H% = 7.70; N% = 11.89; Found: C, 71.38; H, 7.62; N, 11.69

III.

D-6-methyl-8β-(phenylcarbamoylmethyl)-9,10-didehydroergoline.

m.p. 223°–226°C (methanol) $[\beta]_D^{20} = +16.5°$ (c=1, $C_5H_5N$), UV (MeOH) 309 nm ($\epsilon$ =8300) ; 232 nm ($\epsilon$ =40700); IR (CHCl$_3$): 1735, 1601 cm$^{-1}$.

For $C_{23}H_{23}N_3O_2$ (373.5) Calcd. C% = 73.97; H% 6.21; N% = 11.25; Found: C, 74.02; H, 6.20; N, 11.44

IV.
D-6-methyl-8β-(N,N-dimethylcarbamoylmethyl)-9,10-dihydroergoline.

m.p. 160°—162°C (benzene) $[\alpha]_D^{20} = +38.9°$ (c=1, $C_5H_5N$); UV (MeOH)=312 nm (ε=8300); IR (KBr) = 1687, 1602 cm$^{-1}$.

For $C_{19}H_{23}N_3O_2$ (325.4) Calcd. C%=70.13; H%=7.12; N%=12.91; Found: C, 70.31; H, 7.11; H, 12.86

V.
D-6-methyl-8β-(N,N-diethylcarbamoylmethyl)-9,10-didehydroergoline.

m.p. 110°–118°C (benzene) $[\beta]_D^{20} = +43.2°$ (c=0.5, $C_5H_5N$): 305 nm (ε=8600); IR (NaCl): 1672, 1608 cm$^{-1}$.

For $C_{21}H_{27}N_3O_2$ (353.5) Calcd. C%=71.36; H%=7.70; N%=11.89; Found: C, 71.37; H, 7.45; N, 11.48

VI
D-6-methyl-8β-(1-adamantylcarbamoylmethyl)-9,10-didehydroergoline.

m.p. 243°+249°C (benzene) $[\alpha]_D^{20} = +23.2°$ (c=1.3, $C_5H_5N$); UV (MeOH) 298 nm (ε= 10300); 243 -(perhydroazoninylcarbonyloxymethyl)-nm (ε= 17350); IR (KBr): 1730, 1602, 3480 cm$^{-1}$.

For $C_{27}H_{33}N_3O_2$ (431.6) Calcd. C%= 75.14; H%=7.71; N%=9.74; Found: C, 75.06; H, 7.55; N, 9.80

VII.
D-6-methyl-8β-(perhydroazoninylcarbonyloxymethyl)-9,10-didehydroergoline.

m.p. 175°–177°C (EtOAc) $[\alpha]_D^{20} = +41.3°$ (c=0.5, $C_5H_5N$), UV (MeOH) 314 nm (ε=9240); IR (CHCl$_3$) 1680, 1605 cm$^{-1}$.

For $C_{25}H_{33}N_3O_2$ (407.6) Calcd. C%=73.68; H%=8.16; N%=10.31: Found: C, 73.59; D, 8.51; N, 10.20

VIII.
D-6-methyl-8β-(azetidinylcarbonyloxymethyl)-9,10-didehydroergoline.

m.p. 218°–221°C (benzene) $[\alpha]_D^{20} = +36.5°$(c=1.0, $C_5H_5N$); UV (MeOH) 313 nm (ε=8150), 242 nm (ε=17450); IR (CHCl$_3$); 1690, 1603, 3360 cm$^{-1}$.

For $C_{20}H_{23}N_3O_2$ (337.40) Calcd. C%=71.19; H%=6.87; N%=12.45 Found: C, 71.26; H, 6.83; N, 12.55

IX.
D-6-methyl-8β-(propylaminocarbonyloxymethyl)-9,10-didehydroergoline.

m.p. 173°–175°C (benzene) $[\alpha]_D^{20} = +26.5°$(c=0.7, $C_5H_5N$); UV (MeOH) 311 nm (ε=8920), 242 nm (ε=21300), IR (CHCl$_3$), 1603, 1705, 3360 cm$^{-1}$ For $C_{20}H_{25}N_3O_2$ (339.4) Calcd. C%=70.77; H%=7.42; N% =12.38; Found: C, 70.62; H, 7.21; N, 12.23.

X. D-6-methyl-8β-pyrrolydylcarbonyloxymethyl)-9,10-didehydroergoline.

m.p. 232°–234°C (benzene); $[\alpha]_D^{20} = +34°$(c=1, $C_5H_5N$), UV (MeOH) 311 nm (ε=8900) 241 nm (ε=18950); IR (CHCl$_3$); 1603, 1682, 3380 cm$^{-1}$ For $C_{21}H_{25}H_3O_2$ (351.5) Calcd. C%=71.77; H%=7.17; N%=11.96 Found: C, 71.91; H, 7.17; N, 11.94

XI. D-6-methyl-8β-(piperidinocarbonyloxymethyl)-9,10-didehydroergoline.

m.p. 240°–242°C (benzene-petroleum ether) $[\alpha]_D^{20} = +30.4°$(c=1, $C_5H_5N$); UV (MeOH); 312 nm (ε=8230); IR (KBr) 1601, 1684 cm$^{-1}$.

For $C_{22}H_{27}N_3O_2$ (365.5) Calcd. C%=72.38; H%=7.45; N%=11.50 Found: C, 72.00; H, 7.37; N, 11.22

XII.
D-6-methyl-8β-(perhydroazepinylcarbonyloxymethyl)-9,10-didehydroergoline.

m.p. 203°–205°C (benzene-petroleum ether; $[\alpha]_D^{20} = +40.8°$. (c=1, $C_5H_5N$); UV (MeOH) 311 nm (ε=8000), 241 nm (ε=18420) IR (CHCl$_3$): 1605, 1680, 3480 cm$^{-1}$.

For $C_{23}H_{29}N_3O_2$ (379.5) Calcd. C%=72.79; H%=7.70; N%=11.07; Found: C, 72.81; H, 7.53; N, 11.16

XIII.
D-6-methyl-8β-(perhydroazocinylcarbonyloxymethyl)-9,10-didehydroergoline.

m.p. 175°–178°C (ethyl acetate) $[\alpha]_D^{20} = +44.3°$(c=1, $C_5H_5N$) UV (MeOH) 312 nm (ε=9350); IR (KBr): 1685, 1735 cm$^{-1}$ For $C_{24}H_{31}N_3O_2$ (393.5) Calcd. C%=73.25; H%=7.94; N%=10.68; Found: C, 73.10; H, 8.15; N, 10.42

XIV.
D-6-methyl-8β-(Δ$^3$-piperidinocarbonyloxymethyl)-9,10-didehydroergoline.

m.p. 221°–223°C (methanol); $[\alpha]_D^{°} = -70°$ (c=1, $C_5H_5N$) UV (MeOH) 312 nm (ε=8790); IR (KBr): 1601, 1660, 1682 cm$^{-1}$ For $C_{22}H_{25}N_3O_2$ (363.5) Calcd. C%=72.70; H%=6.93; N%=11.56; Found; C, 72.57; H, 6.85; N, 11.27

XV. D-6-methyl-8β-morpholinocarbonyloxymethyl)-9,10-didehydroergoline.

m.p. 201°–203°C (methanol)-$\alpha]_D^{20} = +37.5°$ (c=1, $C_5H_5N$); UV (MeOH) 312 nm (ε=8950); IR (KBr or CHCl$_3$); 1602, 1689 cm$^{-1}$ For $C_{21}H_{25}N_3O_2$ (367.5) Calcd. C%=68.64; H%=6.86; N%=11.44; Found: C, 68.50; H, 6.82; N, 11.33

XVI.
D-6-methyl-8β-(4-methylpiperazinylcarbonyloxymethyl)-9,10-didehydroergoline.

m.p. 256°–257°C (CHCl$_3$+(CH$_3$)$_2$CO), $[\alpha]_D^{20} = +35.5°$(c=1, $C_5H_5N$) UV (MeOH) 312 nm (ε=8550); IR (KBr) 1601, 1687 cm$^{-1}$ For $C_{22}H_{28}N_4O_2$ (380.5) Calcd. C%=69.45; H%=7.42; N%=14.72; Found: C, 69.14; H, 7.16; N, 14.42

XVII
D-6-methyl-8β-(4-phenyl-piperazinylcarbonyloxymethyl)-9,10-didehydroergoline.

m.p. 167°–169°C (benzene) $[\alpha]_D^{20}$ = +32.5° (c=1, $C_5H_5N$) UV (MeOH) 312 nm (ε =8600); IR (KBr) 1600, 1684 cm$^{-1}$ For $C_{27}H_{30}N_4O_2$ (442.6) Calcd. C%=73.28; H%=6.83; N%=12.66; Found: C, 73.63; H, 6.87; N, 12.48

XVIII.
D-6-methyl-8β-(veratrylaminocarbonyloxymethyl)-9,10-didehydroergoline.

m.p. 148°–152°C (methanol) $[\alpha]_D^{20}$ = +25.2° (c=1, $C_5H_5N$) UV (tartrate) (MeOH) 312 nm (ε =8600), 287 nm (ε =8070) IR (KBr): 1720, 1305, 1590, 1265 cm$^{-1}$.

For $C_{30}H_{35}N_3O_{10}$ (597.6) Calcd. C%=60.29; H%=5.90; N%=7.03; Found: C, 60.44; H, 6.23; N, 7.33

XIX. D-6-methyl-8β-(pyridyl-3-methylaminocarbonyloxymethyl)-9,10-didehydroergoline.

m.p. 175°–176°C (benzene) $[\alpha]_D^{20}$ = +31° (c=1, $C_5H_5N$) UV (MeOH) 312 nm (ε =7660); IR (KBr) = 1710, 1596, 1580, 1500 cm$^{-1}$ For $C_{23}H_{24}N_4O_2$ (388.5) Calcd. C%=71.11; H%=6.23; N%=14.42; Found: C, 70.80; H, 6.13; N, 14.16

XX.
D-6-methyl-8β-(phenethylaminocarbonyloxymethyl)-9,10-didehydroergoline.

m.p. 140°–142°C (benzene); $[\alpha]_D^{20}$ = +19.3° (c=1, $C_5H_5N$) UV (MeOH) 312 nm (ε =8840); IR (CHCl$_3$); 1604, 1715 cm$^{-1}$ For $C_{25}H_{27}N_3O_2$ (401.5) Calcd. C%=74.79; H%=6.78; N%=10.47; Found: C, 74.75; H, 6.68; N, 10.36

XXI.
D-6-methyl-8β-(2-morpholinoethylaminocarbonyloxymethyl)-9,10-didehydroergoline.

m.p. 186°–188°C (methanol); $[\alpha]_D^{20}$ = +26.6° (c=1, $C_5H_5N$) UV (MeOH) 312 nm (ε =8460); IR (KBr) 1603, 1720 cm$^{-1}$.

For $C_{23}H_{30}N_4O_3$ (410.5) Calcd. C%=67.29; H%=7.37; N%=13.65; Found: C, 67.41; H, 7.01; N, 13.65

XXII.
D-6-methyl-8β-(piperonylmethylaminocarbonyloxymethyl)-9,10-didehydroergoline.

m.p. 182°–183°C (methanol) $[\alpha]_D^{20}$ = +40.2° (c=1, $C_5H_5N$) UV (MeOH) 314 nm (ε =8860), 292 nm, (ε =10030) IR (CHCl$_3$); 1712, 1678, 1605, 1245 cm$^{-1}$ For $C_{26}H_{27}N_3O_4$ (445.5) Calcd. C%=70.10; H%=6.11; N%=9.43; Found: C, 70.00; H, 6.01; N, 9.53

XXIII.
D-6-methyl-8β-(3,4-dihydroxyphenethylaminocarbonyloxymethyl)-9,10-didehydroergoline.

m.p. 140°–150°C (ethyl acetate-benzene) $[\alpha]_D^{20}$ = +15.1° (c=0.5, $C_5H_5N$); UV (MeOH) 290–317 nm (ε =7960); IR (KBr): 1700, 1603, 3380, 3450 cm$^{-1}$ For $C_{25}H_{27}N_3O_4$ (433.50) Calcd. C%=69.27; H%=6.28; N%=9.69; Found: C, 68.84; H, 6.42; N, 9.49

XXIV.
D-6-methyl-8β-(3,4-dimethoxyphenethylaminocarbonyloxymethyl)-9,10-didehydroergoline.

m.p. 75°–80°C (acetonitrile) $[\alpha]_D^{20}$ = +23.9° (c=1, $C_5H_5N$) UV (MeOH) 312 nm (ε =7600), 287 nm (ε =6880) IR (KBr): 1690, 1606, 1590, 1265 cm$^{-1}$ For $C_{27}H_{31}N_3O_4$ (461.6) Calcd. C%=70.26; H%=6.77; N%=9.10; Found: C, 70.25; H, 6.60; N, 9.09

XXV.
D-6-methyl-8β-(α-methylphenethylaminocarbonyloxymethyl)-9,10-didehydroergoline.

m.p. 197°–199°C (ethanol) $[\alpha]_D^{20}$ = +38.2° (c=1, $c_5H_5N$) UV (tartrate) (MeOH) 314 nm (ε =7850), 240 nm, (ε =17850) IR (CHCl$_3$): 1602, 1700 cm$^{-1}$ For $C_{26}H_{29}N_3O_2$ · ½ $C_4H_6O_6$ (490.6) Calcd. C%=68.55; H%=6.57; N%=8.56; Found: C, 69.02; H, 6.53; N, 8.81

XXVI
D-6-methyl-8β-(triptaminylcarbonyloxymethyl)-9,10-didehydroergoline.

m.p. 143°–145°C (benzene-petroleum ether) $[\alpha]_D^{20}$ = +16.3° (c=1, $C_5H_5N$); UV (MeOH) 312 nm (ε =7400), 293 nm (ε =10350), 285 nm (= 9600); IR (CHCl$_3$); 1715, 1606, 3380, 3530 cm$^{-1}$ For $C_{27}H_{28}N_4O_2$ (440.5) Calcd. C%=73.61; H%=6.41; N%=12.72; Found: C, 73.65; 6.17; N, 13.02

XXVIII. D-6-methyl-8β-(carbamoylmethyl)-ergoline.

m.p. 248°–250°C (methanol) $[\alpha]_D^{20}$ = –87.8° (c=1, $C_5H_5N$) UV (MeOH): 293 nm (ε =5200), 282 nm (ε =6350) IR (KBr): 1700, 1605 cm$^{-1}$ For $C_{17}H_{21}N_3O_2$ (299.4) Calcd. C%=68.21; H%=7.07; N%=14.04; Found: C, 68.30; H, 6.90; N, 14.04

XXVIII. D-6-methyl-8β-sec.butylaminocarbonyloxymethyl)-ergp;ome/ m.p. 165°–166°C (benzene-petroleum ether) $[\alpha]_D^{20}$ = –59,7° (c=1, $C_5H_5N$); UV(MeOH) 292 nm (ε =5350), 28⁷ nm (ε =6650); IR (KBr): 1690, 1809 cm$^{-1}$ For $C_{21}H_{29}N_3O_2$ (355.5) Calcd. C%=70.96; H%=8.22; N%=11.82; Found: C, 70.91; H, 8,19; N, 11.71

XXIX.
D-6-methyl-8β-(phenylcarbamoylmethyl)-ergoline.

m.p. 245°–247°C (methanol); $[\alpha]_D^{20}$ = –75.4° (c=1, $C_5H_5N$) UV (MeOH); 292 nm (ε =6130), 282 nm (ε =7840), 225 nm (ε =43100); 210 nm (ε =51000); IR (CHCl$_3$); 1732, 1603 cm$^{-1}$.

For $C_{23}H_{25}N_3O_2$ (375.5) Calcd. C%=73.58; H%=6.71; N%=11.19, Found: C, 73.43; H, 6.66; N, 11.20

XXX.
D-6-methyl-8β-(N,N-dimethylcarbamoylmethyl)-ergoline.

m.p. 245°–247°C (methanol) $[\alpha]_D^{20}$ = –82.4° (c=1, $C_5H_5N$) UV (MeOH): 292 nm (ε =4750), 282 nm (ε =5780), 215 nm (ε =49600); IR (CHCl$_3$); 1685, 1610 cm$^{-1}$ For $C_{19}H_{25}N_3O_2$ (327.4) Calcd. C%=69.70; H%=7.70; N%=12.84; Found: C, 69.80; H, 7.71; N, 12.87

XXXI.
D-6-methyl-8β-(N,N-diethylcarbamoylmethyl)-ergoline.

m.p. 153°–155°C (ethyl acetate) $[\alpha]_D^{20} = -69.2°$ (c=0.5, $C_5H_5N$); UV (MeOH): 292 nm ($\epsilon$=5240), 282 nm ($\epsilon$=5800) IR (KBr): 1692 cm$^{-1}$ For $C_{21}H_{29}N_3O_2$ (355.5) Calcd. C%=70.96; H%=8.22; N%=11.82; Found: C, 70.22; H, 8.23; N, 11.57

XXXII.
D-6-methyl-8β-(1-adamantylcarbamoylmethyl)-ergoline.

m.p. 279°–280°C (benzene-petroleum ether). $[\alpha]_D^{20} = -80.6°$ (c=1.2, $C_5H_5N$); UV (MeOH): 292 nm ($\epsilon$=5150), 282 nm ($\epsilon$=6070); IR (KBr): 1728, 1603 cm$^{-1}$ For $C_{27}H_{35}N_3O_2$ (433.6) Calcd. C%=74.79; H%=8.14; N%=9.69; Found: C, 74.66; H, 8.04; N, 9.56

XXXIII.
D-6-methyl-8β-(perhydroazoninylcarbonyloxymethyl)-ergoline.

m.p. 157°–160°C (methanol); $[\alpha]_D^{20} = -59.0°$ (c=0.55, $C_5H_5N$) UV (MeOH): 292 nm ($\epsilon$=5650); 282 nm ($\epsilon$=6850), 226 nm ($\epsilon$=32200); IR ($CHCl_3$): 1675 cm$^{-1}$ For $C_{25}H_{35}N_3O_2$ (409.6) Calcd C%=73.31; H%=8.61; N%=10.26; Found: C, 72.98; H, 8.79; N, 10.11

XXXIV.
D-6-methyl-8β-(azetidinylcarbonyloxymethyl)-ergoline.

m.p. 228°–229°C (methanol)-$[\alpha]_D^{20} = -76.5°$ (c=1, $C_5H_5N$) UV (MeOH): 292 nm ($\epsilon$ = 6640); IR (KBr) 1688, 1601, 3480 cm$^{-1}$ For $C_{20}H_{25}N_3O_2$ (339.40) Calcd. C%=70.77; H%=7.42; N%=12.38; Found: C, 70.75; H, 7.40; N, 12.43

XXXV.
D-6-methyl-8β-(propylaminocarbonylmethyl)-ergoline.

m.p. 174°–176°C (benzene-petroleum ether) $[\alpha]_D^{20} = -75.0°$ (c=1.3, $C_5H_5N$); UV (MeOH); 293 nm ($\epsilon$=5330); 282 nm (=6500) 178 nm ($\epsilon$=6180); IR (Kbr): 1698, 1606, 3380 cm$^{-1}$ For $C_{20}H_{27}N_3O_2$ (341.5) Calcd. C%=70.35; H%=7.97; N%=12.39; Found: C, 70.30; H, 7.67; N, 12.69

XXXVI.
D-6-methyl-8β-(pyrrolidylcarbonyloxymethyl)-ergoline.

m.p. 216°–218°C (benzene)-$[\alpha]_D^{20} = -78.2°$ (c=1, $C_5H_5N$) UV (MeOH): 292 nm ($\epsilon$=5150), 282 nm ($\epsilon$=6320), 225 nm ($\epsilon$=55650); IR ($CHCl_3$): 1680, 1608 cm$^{-1}$ For $C_{21}H_{27}N_3O_2$ (353.5) Calcd. C%=71.36; H%=7.70; N%=11.89; Found: C, 71.52; H, 7.58; N, 11.80

XXXVII.
D-6-methyl-8β-(piperidinocarbonyloxymethyl)-ergoline.

m.p. 237°–238°C (methanol)-$[\alpha]_D^{20} = -59°$ (c=1, $C_5H_5N$) UV (MeOH): 292 nm ($\epsilon$=5350); 282 nm ($\epsilon$=6660) IR (KBr): 1682, 1618, 1605, 3480 cm$^{-1}$ For $C_{22}H_{29}N_3O_2$ (367.5) Calcd. C%=71.90; H%=7.95; N%=11.43; Found: C, 72.08; H, 7.92; N, 11.48

XXXVIII.
D-6-methyl-8β-(perhydroazepinylcarbonyloxymethyl)-ergoline.

m.p. 171°–173°C (methanol)-$[\alpha]_D^{20} = -61.5°$ (c=1, $C_5H_5N$) UV (MeOH): 292 nm ($\epsilon$=5340), 282 nm ($\epsilon$=6600), 222 nm ($\epsilon$=34300); IR (KBr): 1680, 1603 cm$^{-1}$ For $C_{23}H_{31}N_3O_2$ (381.5) Calcd. C%=72.41; H%=8.19; N%=11.01; Found: C, 72.33; H, 8.04; N, 11.04

IXL.
D-6-methyl-8β-(perhydroazocinylcarbonyloxymethyl)-ergoline.

m.p. 210°–212°C (ethanol)-$[\alpha]_D^{20} = -63.0°$ (c=1, $C_5H_5N$) UV (MeOH); 292 nm ($\epsilon$=5500), 282 nm ($\epsilon$=6670), 226 nm ($\epsilon$=28100); IR (KBr): 1690 cm$^{-1}$ For $C_{24}H_{33}N_3O_2$ . ½ $C_4H_6O_6$ (470.5): Calcd. C%=66.36; H%=7.71; N%=8.94; Found: C, 66.41; H, 7.82; N, 8.98

XL.
D-6-methyl-8β-(Δ³-piperidinocarbonyloxymethyl)-ergoline.

m.p. 213°–215°C (benzene) $[\alpha]_D^{20} = -70°$ (c=1, $C_5H_5N$) UV MeOH): 292 mn ($\epsilon$=5300), 282 nm ($\epsilon$=6780) IR ($CHCl_3$): 1685, 1660, 1610 cm$^{-1}$ For $C_{22}H_{27}N_3O_2$ (365.5) Calcd. C%=72.30; H%=7.45; N%=11.50; Found: C, 72.45; H, 7.24; N, 11.28

XLI.
D-6-methyl-8β-(morpholinocarbonyloxymethyl)-ergoline.

m.p. 194°–195°C (benzene) $[\alpha]_D^{20} = -72°$ (c=1, $C_5H_5N$) UV (MeOH): 292 nm ($\epsilon$=5430), 282 nm ($\epsilon$=6920) IR (KBr): 1690, 1612, 1470 cm$^{-1}$ For $C_{21}H_{27}N_3O_2$ (369.5) Calcd. C%=68.27; H%=7.37; N%=11.37; Found: C, 68.16; H, 7.20; N, 11.36

XLII.
D-6-methyl-8β-(4-methyl-piperazinylcarbonyloxymethyl)-ergoline.

m.p. 268°–270°C ($CHCl_3$—$(CH_3)_2$—CO) $[\alpha]_D^{20} = -71.8°$ (c=1, ($C_5H_5N$); UV (MeOH): 292 nm ($\epsilon$=5130), 282 nm ($\epsilon$=6230); IR (KBr): 1685, 1605 cm$^{-1}$ For $C_{22}H_{30}N_4O_2$ (382.5) Calcd. C%=69.08; H%=7.91; N%=14.65; Found: C, 68.82; H, 7.55; N, 14.40

XLIII.
D-6-methyl-8β-(4-phenyl-piperazinylcarbonyloxymethyl)-ergoline.

m.p. 178°–180°C (benzene) $[\alpha]_D^{20} = -61.3°$ (c=1, $C_5H_5N$) UV (MeOH + 5% $CHCl_3$): 292 nm ($\epsilon$=6940), 282 nm ($\epsilon$=8000); IR (KBr): 1685, 1600 cm$^{-1}$ For C$_{27}$H$_{32}$N$_4$O$_2$ (444.6) Calcd. C%=72.95; H%=7.26; N%=12.60; Found: C, 73.09; H, 7.00; N, 12.49

XLIV.

D-6-methyl-8β-(veratrylaminocarbonyloxymethyl)-ergoline.

m.p. 158°–160°C (ethyl acetate) $[\alpha]_D^{20} = -53.7°$ (c=1, C$_5$H$_5$N); UV (MeOH): 292 nm (∈=5130), 282 nm (∈=9500); IR (KBr): 1712, 1608, 1590, 1260 cm$^{-1}$ For C$_{26}$H$_{31}$N$_3$O$_4$ (449.6) Calcd. C%=69.47; H%=6.95; N%=9.35; Found: C, 69.42; H, 6.84; N, 9.41

XLV.

D-6-methyl-8β-(pyridyl-3-methylaminocarbonyloxymethyl)-ergoline.

m.p. 139°–141°C (methanol) $[\alpha]_D^{20} = -59.4°$ (c=1, C$_5$H$_5$N) UV (MeOH): 292 nm (∈=5520), 282 nm (∈=5960), 275 nm (∈=10.200), 265 nm (∈=10.400), 259 nm (∈=10300); IR (KBr): 1720, 1610, 1580, 1500 cm$^{-1}$ For C$_{23}$H$_{26}$N$_4$O$_2$ (390.5) Calcd. C%=70.75; H%=6.71; N%=14.35; Found: C, 70.77; H, 6.87; N, 14.37

XLVI.

D-6-methyl-8β-(phenethylaminocarbonyloxymethyl)-ergoline.

m.p. 155°–156°C (methanol) $[\alpha]_D^{20} = -60.2°$ (c=1, C$_5$H$_5$N) UV (MeOH): 292 nm (∈=5080), 282 nm (∈=6100) IR (KBr): 1695, 1610 cm$^{-1}$ For C$_{25}$H$_{29}$N$_3$O$_2$ (403.5) Calcd. C%=74.41; H%=7.24; N%=10.41; Found: C, 74.52; H, 7.27; N, 10.37

XLVII.

D-6-methyl-8β-(2-morpholinoethylaminocarbonyloxymethyl)-ergoline.

m.p. 146°–148°C (methanol) $[\alpha]_D^{20} = -56.3°$ (c=1, C$_5$H$_5$N); UV (MeOH): 292 nm (∈=5310), 282 nm (∈=6530) IR (KBr): 1698, 1606 cm$^{-1}$ For C$_{23}$H$_{32}$N$_4$O$_3$ (412.5) Calcd. C%=66.97; H%=7.82; N%=13.58; Found: C, 66.61; H, 7.75; N, 13.35

XLVIII.

D-6-methyl-8β-(piperonylmethylaminocarbonyloxymethyl)-ergoline.

m.p. 176°–177°C (methanol) $[\alpha]_D^{20} = -48.7°$ (c=1, C$_5$H$_5$N) UV (MeOH): 292 nm (∈=5130), 282 nm (∈=10600); IR (KBr): 1712, 1680, 1608, 1245 cm$^{-1}$ For C$_{26}$H$_{29}$N$_3$O$_4$ (447.5) Calcd. C%=69.78; H%=6.53; N%=9.39; Found: C, 69.65; H, 6.39; N, 9.47

IL.

D-6-methyl-8β-(3,4-dihydroxyphenethylaminocarbonyloxymethyl)-ergoline.

m.p. 168°–175°C (methanol) $[\alpha]_D^{20} = -12°$ (c=1, C$_5$H$_5$N) UV (MeOH): 292 nm (∈=6450), 283 nm (∈=8140) IR (KBr): 1695, 1603, 3420 cm$^{-1}$ For C$_{25}$H$_{29}$N$_3$O$_4$ . C$_2$H$_4$O$_2$ (479.6): Calcd. C%=65.44; H%=6.71; N%=8.76; Found: C, 65.44; H, 6.71; N, 8.54

L.

D-6-methyl-8β-(3,4-dimethoxyphenethylaminocarbonyloxymethyl)-ergoline.

m.p. 120° (acetone) $[\alpha]_D^{20} = -47.5°$ (c=1, C$_5$H$_5$N) UV (MeOH): 293 nm (∈=5100), 282 nm (∈=9120) IR (KBr): 1690, 1608, 1590, 1260 cm$^{-1}$ For C$_{27}$H$_{33}$N$_3$O$_4$ (463.6 Calcd. C%=69.96; H%=7.18; N%=9.06; Found: C, 68.94; H, 6.90; N, 8.81

LI.

D-6-methyl-8β-(α-methylphenethylaminocarbonyloxymethyl)-ergoline.

m.p. 219°–222°C (methanol) $[\alpha]_D^{20} = -49°$ (c=1, C$_5$H$_5$N) UV (MeOH): 292 nm (∈=5440), 282 (∈=6640) IR (KBr): 1730, 1705, 1608 cm$^{-1}$ For C$_{26}$H$_{31}$N$_3$O$_2$ . ½ C$_4$H$_6$O$_6$ (492.6): Calcd. C%=68.27; H%=6.96; N%=8.53; Found: C, 68.57; H, 7.05; N, 8.72

LII.

D-6-methyl-8β-(tryptaminylcarbonyloxymethyl)-ergoline.

m.p. 200°–202°C (chloroform); $[\alpha]_D^{20} = -62°$ (c=1, C$_5$H$_5$N) UV (MeOH): 292 nm (∈=9350), 282 nm (∈=11150), 276 nm (∈=10630), 220 nm (∈=58700) IR (KBr): 1730, 1698, 1615, 1608, 1550, 1500 cm$^{-1}$ For C$_{27}$H$_{30}$N$_4$O$_2$ (442.6) Calcd. C%=73.28; H%=6.83; N%=12.66; Found: C, 72.89; H, 6.72; N, 13.04

The novel compounds, as obtained according to the present invention, display pharmacological actions on several regions and organs, already at extremely low dosages. It has been found that the novel products unfold effects on the peripheral circulatory system as vasodilatory-agents, on the central nervous system they act as stimulants. The compounds are also endowed with antiserotoninic actions and spasmolytic actions on the gastrointestinal smooth muscles. The active dosages are comprised between 1 and 500 micrograms per kilogram, in vivo.

More particularly, a few of the novel compounds manifest a few of the above enumerated activities in a selective way, so as to make their use possible for the therapeutics.

Actually, the compound XXXVIII, as well as the compounds XXXIII, IXL have shown to have a spasmolytic action which is particularly conspicuous on the isolated smooth muscles of the bowel and the gall bladder in guinea pigs. The active concentrations are comprised between 2 and 20 micrograms per ml. This compound also displays a spasmolytic action on the muscles of the blood vessels in dogs. The range of the active dosages is comprised between 20 and 100 micrograms/kilogram e.v. In vitro, the compound XXXVIII releases the muscles of the aorta of rabbits at concentrations of 50–100 micrograms/ml. The therapeutic index is favourable for an indication of the product as an antispastic of the gastro-intestinal system and the biliary tract.

The compound XXV, in its turn, is endowed with interesting actions which stimulated the central nervous system. On isolated organs (ileum of guinea pigs, deferent vessel of rats) the product displays also a considerable spasmolytic activity, acting at dosages from 1 to 10 micrograms/ml. These effects are displayed also in vivo on the muscles of the peripheral vessels at dosages of 20–200 micrograms/kilogram e.v. The compound LI has been found to have lost the stimulating effects on the central nervous system, whereas the spasmolytic properties on the bowel and vessel muscles, both in vitro and in vivo are retained. The active dosages are comprised between 5 and 20 micrograms/ml in vitro, and from 50 to 500 micrograms/kilogram e.v. The acute toxicity of the compound LI has proven to be extremely low and consequently the therapeutic index is favorable for its use as a spasmolytic of the smooth muscles of the vessels and organs other than vessels.

Lastly, another compound of the series, the IV, has been found to be endowed with a strong peripheral vasoconstrictive hypertensive action, in vivo, in dogs, at dosages comprised between 1 and 50 micrograms/kilogram e.v. and in cats from 6 to 50 micrograms/kilogram e.v. The effect is proportional to the dosage. The compound, on the basis of the tests which have been carried out, is a stimulant of the alpha-adrenergic receptors. In addition, the compound IV acts on the trachea of guinea pigs as a releasing agent at the concentration of 0.5–1 microgram/ml. On the ileum of the same animals, as a spasmolytic at a concentration of 50–100 micrograms/ml and on the uterus and stomach of rats as an antiserotoninic at the concentration of 0.05–0.1 micrograms/ml. These latter effects are displayed also in vivo at the level of the smooth muscles of the vessels (active dosages = 5–10 micrograms/kilogram e.v.) and of the central nervous system (active dosages = 0.5–1 milligrams/kilogram s.c.). The compound on the basis of the pharmacological and toxicological properties which have been detected can be employed for the treatment of headaches.

For the therapeutical use the novel compounds can be employed as such or in the form of appropriate salts with both mineral and organic acids. In addition, they can be appropriately formulated in suitable pharmaceutical compositions in the form of tabloids or dragees or drops for the oral administration, ampoules for the parenteral use, and suppository for the rectal administration. It is also possible to prepare delayed release preparations so as to ensure a therapeutical action which is prolonged in time. For all of these preparations, the fillers and the methods as commonly adopted in the pharmaceutical practice are employed.

The following examples illustrate in more detail the several methods according to the invention for the preparation of the compounds having the formula (I).

EXAMPLE 1 (Method A)

Lysergol ($R_A = R_B = H$, x⎯y = —CH=C<), 40 grams, is dissolved in anhydrous piridine (500 mls) and to the solution, cooled to 0°C with ice, there is added very slowly with stirring phenyl chloroformate (32.8 grams). On completion of the addition the mixture is allowed to reach the room temperature and is maintained stirred during 7 hours. The mixture is then poured over water and ice. The as formed precipitate is washed thoroughly with water, then with methanol, and dried. It is recrystallized from 3500 mls benzene (filtration over carbon) to obtain D-6-methyl-8β-(phenoxycarbonyloxymethyl)-9,10 didehydroergoline, in a state of purity, having a m.p. of 218°–220°C.

The latter compound (100 grams) is dissolved in anhydrous $(CH_3)_2NCHO$ (1670 mls) under a dry nitrogen blanket, in an oxygen-free environment. To this solution there is added perhydroazepine (58.3 grs) at room temperature, whereafter it is heated to 70°–75°C and is maintained at this temperature during 6 hours, still with stirring under a nitrogen blanket. The precipitate is poured over ice and water (10 liters), collected on a filter, washed with water on the filter. It is dried over $P_2O_5$, and, upon drying, it is recrystallized from benzene (1500 mls) (filtration over carbon).

Pure D-6-methyl-8β-(perhydroazepinylcarbonyloxymethyl)-9,10-didehydroergoline (XII) is thus obtained, with a m.p. 203°–205°C, $[\alpha]_D^{20} = +40.8°$ (in $C_5H_5N$).

EXAMPLE 2 (Method A)

D-6-methyl-8β-(phenoxycarbonyloxymethyl)-9,10-didehydro-ergoline (12 grs.) is dissolved in anhydrous $Me_2SO$ (200 mls) under dry nitrogen and in the absence of oxygen. To this solution there is added α-methylphenethylamine (9.6 grs.) in anhydrous $Me_2SO$ (10 mls) at room temperature and the mixture is maintained at 70°–75°C during 5 hours with a slight stirring. The mixture is poured over ice and water and the precipitate is collected on a filter and thoroughly washed with water on the filter. Upon drying over $P_2O_5$ in a vacuo, the product is recrystallized with 200 mls of benzene (filtered over activated carbon) and 300 mls. petroleum ether. The crystallized product is filtered through a silica-gel column (80 grs) eluting it with a mixture of benzene plus 3% methanol to discharge the color. The eluates are concentrated to a reduced volume and the product is separated in the form of tartrate. This is obtained by adding to the solution one molar equivalent of tartaric acid. The as separated tartrate is filtered and dried in a vacuo. It is purified by recrystallizing it from absolute ethanol. The salt, bis [D-6-methyl-8β-(α-methylphenetylaminocarbonyloxymethyl)-9,10-didehydroergoline] tartrate (XXV) has a m.p. 197°–199°C, $[\alpha]_D^{20} = +38.2$ ($C_5H_5N$).

Similarly to the compound of the Examples 1, 2, the compounds I, II, IV-XXVIII, XXX-LII are prepared. In this case of the compounds XXVII and following, the starting compounds are substance of general formula (I) wherein $R_A=R_B=H$, x⎯y = —CH_2—CH<.

EXAMPLE 3 (Method B)

To a suspension of lysergol ($R_A=R_B=H$, x⎯y = —CH=C<) (10 grs) in anhydrous benzene (250 mls) there is added, with stirring, phenyl isocyanate (6.15 grs) and the whole is refluxed with stirring during 7 hours. The as formed product is cooled and collected on a filter, washed with benzene and then with gasoline. (The waters are evaporated to dryness and the residue taken up with ether and filtered; the precipiate is combined with the principal precipitate indicated above). Crystallization is carried out with acetone (600 mls) (filtration on carbon) giving a yield of 11.5 grs of D-6-methyl-8β-(phenylcarbamoylmethyl)-9,10-didehydroergoline, having a m.p. 223°–226°C; $[\alpha]_D^{20} = +16.5$ ($C_5H_5N$).

EXAMPLE 4 (Method C)

D-6-methyl-8β-(morpholinocarbonyloxymethyl)-9,10-didehydroergoline (XV), 3.0 grs. ($R_A = $ —$CON(CH_2)_2O$, $R_B = H$, x⎯y = —CH=C<) is dissolved in a mixture of anhydrous EtOH and the 10% of acetic acid, (70 mls) and there are added 1.2 grams of 10% palladated carbon. Hydrogenation is carried out in a Parr type apparatus with an initial pressure of hydrogen of about 3 atmospheres. Upon consumption of 197 mls of $H_2$ (40 minutes approx.) the reactor is scavenged with nitrogen, the catalyst is collected on a filter and the alcohol evaporated in a vacuo (25 mmsHg) at a temperature below 50°C. The residue is diluted with water, neutralized with NaHCO$_3$, the precipitate is collected on a filter and washed on the filter with water, methanol and ether. This raw product for purification is dissolved in 60 mls methanol, treated with activated carbon and filtered. Upon two crystallizations one obtains D-6-methyl-8β -(morpholinocarbonyloxymethyl)-ergoline (XLI, 2.3 grs), m.p. 194°–195°C, $[\alpha]_D^{20}$ = −72° (c=1, C$_5$H$_5$N).

According to what has been suggested in Example 4, the compounds Nos. XXVII–IXL, XLI–LII are prepared.

With the above indicated methods, all the previously enumerated compounds from I to LII have been prepared.

The embodiments of the invention in which an exclusive property or privilege is claimed are defined as follows:

1. D-6-methyl-8β-(N,N-dimethylcarbamoylmethyl)-9,10-didehydroergoline.
2. D-6-methyl-8β-(N,N-diethylcarbamoylmethyl)-9,10-didehydroergoline.
3. D-6-methyl-8β-(1-adamantylcarbamoylmethyl)-9,10-didehydroergoline.
4. D-6-methyl-8β-(perhydroazoninylcarbonyloxymethyl)-9,10-didehydroergoline.
5. D-6-methyl-8β-(pyrrolidylcarbonyloxymethyl)-9,10-didehydroergoline.
6. D-6-methyl-8β-(piperidinocarbonyloxymethyl)-9,10-didehydroergoline.
7. D-6-methyl-8β-(perhydroazocynylcarbonyloxymethyl)-9,10-didehydroergoline.
8. D-6-methyl-8β-(Δ$^3$-piperideinocarbonyloxymethyl)-9,10-didehydroergoline.
9. D-6-methyl-8β-(pyridyl-3-methylaminocarbonyloxymethyl)-9,10-didehydroergoline.
10. D-6-methyl-8β-(piperonylmethylaminocarbonyloxymethyl)-9,10-didehydroergoline.
11. D-6-methyl-8β-(triptaminylcarbonyloxymethyl)-9,10-didehydroergoline.
12. D-6-methyl-8β-(N,N-dimethylcarbamoylmethyl)-ergoline.
13. D-6-methyl-8β-(N,N-diethylcarbamoylmethyl)-ergoline.
14. D-6-methyl-8β-(1-adamantylcarbamoylmethyl)-ergoline.
15. D-6-methyl-8β-(perhydroazoninylcarbonyloxymethyl)-ergoline.
16. D-6-methyl-8β-(pyrrolidylcarbonyloxymethyl)-ergoline.
17. D-6-methyl-8β-(piperidinocarbonyloxymethyl))-ergoline.
18. D-6-methyl-8β-(perhydroazocynylcarbonyloxymethyl)-ergoline.
19. D-6-methyl-8β-(Δ$^3$-piperideinocarbonyloxymethyl)-ergoline.
20. D-6-methyl-8β-(pyridyl-3-methylaminocarbonyloxymethyl)-ergoline.
21. D-6-methyl-8β-(piperonylmethylaminocarbonyloxymethyl)-ergoline.
22. D-6-methyl-8β-(triptaminylcarbonyloxymethyl)-ergoline.
23. D-6-methyl-8β-(azetidinylcarbonyloxymethyl)-9,10-didehydroergoline.
24. D-6-methyl-8β-(perhydroazepinylcarbonyloxymethyl)-9,10-didehydroergoline.
25. D-6-methyl-8β-(azetidinylcarbonyloxymethyl)-ergoline.
26. D-6-methyl-8β-(perhydroazepinylcarbonyloxymethyl)-ergoline.

* * * * *